United States Patent [19]

Bergfeld et al.

[11] 4,255,420
[45] Mar. 10, 1981

[54] HORMONE COMBINATION AND METHOD FOR STIMULATION OF OVULATION

[75] Inventors: Jost Bergfeld, Dummerstorf; Marie-Luise Raasch, Rostock; Ingo König, Dummerstorf; Klaus-Peter Brüssow, Rostock, all of German Democratic Rep.

[73] Assignee: VEB Berlin-Chemie, Berlin, German Democratic Rep.

[21] Appl. No.: 109,688

[22] Filed: Jan. 4, 1980

[30] Foreign Application Priority Data

Dec. 29, 1978 [DD] German Democratic Rep. ... 210247

[51] Int. Cl.³ ............................................. A61K 37/00
[52] U.S. Cl. ................................................... 424/177
[58] Field of Search ........................................ 424/177

[56] References Cited

U.S. PATENT DOCUMENTS 4,196,123  4/1980  Rosemberg ................. 260/112.5 R Primary Examiner—Delbert R. Phillips
Attorney, Agent, or Firm—Michael J. Striker

[57] ABSTRACT

The invention is a process for ovulation stimulation in which a combination of two known hormones or preparations, HCG and Gn-RH, are used to regulate the reproductive process. The mixing occurs in a preferably isotonic medium through the use of IE units for HCG and $\mu$g for Gn-RH, according to the current applicable DDR standards.

The combination preparation can be used for biotechnical and/or therapeutic stimulation and release of ovulation in female culture animals, such as swine, sheep, cattle, horses, and fish, and other domesticated or luxury animals, such as cats, dogs, zoo animals and ornamental fish. The administration should occur in the stage prior to heat, in the fertile period or during the spawning stage.

3 Claims, No Drawings

HORMONE COMBINATION AND METHOD FOR STIMULATION OF OVULATION

BACKGROUND OF THE INVENTION

The invention concerns a hormone combination for the stimulation of ovulation for hormonal control of the reproduction process in the raising of animals, and a method for the use of this combination.

Ovulation is physiologically induced through the hormone of the pituitary—hypophyse. Hypophyse is in turn regulated through control centers in the hypothalamus. (Doecke 1975)

For biotechnical and therapeutic stimulation and release of ovulation in animals, additional hormones are injected; these are derived from the serum of pregnant mares—PMSG—and the urine of pregnant women—HCG. If the injections are carried out simultaneously in a group of animals, an ovulation synchronization is effected, which can be employed in a wide range of contexts, such as in swine raising. (Huehn and coworkers, 1974; Prange and Bergfeld 1975; TGL No. 31709 Gr. 941250).

In these processes, the animals are first presynchronized, then treated with PMSG and finally with HCG prior to two artificial inseminations. The ovulation follows after about 42 hours from the HCG injection, but there is considerable variation, so that at a fixed insemination time not all cells are fertilized. Moreover, as PMSG and HCG are foreign protein preparations, with multiple applications the development of immunity cannot be completely excluded.

The gonadotropins PMSG and HCG enter the blood circulation after the injections and acts directly upon the ovaries. They thereby override or increase the activity of the hormones produced by the animals themselves. As the biotechnical control of the reproduction process makes possible a more intensive production of animal stocks, the range of applicability of the method of ovulation stimulation or release is quite broad. The possibilities of production for the required biological active substances, however, is limited and thus reduces the actual applications of the process.

DESCRIPTION OF THE INVENTION

The invention is directed to the development of a technique which combines the stimulating activity of hypophyse produced by the organism itself and the known activity of the exogenous HCG introduced into the organism. The endogenexogen combination effect should lead to the following advantages over the conventional methods:

1. Stabilization and improvement of the treatment effects in ovulation stimulation, and thereby an increase in fertility rates, the achievement of therapeutic effects, better synchronization of ovulation and reduction in the amount of sperm required through simplified insemination.

2. Reduction in the amount of HCG to be administered per animal.

3. Reduction in the danger of the development of an immunity towards HCG.

Through a combination of two preparations which are in themselves known, the invention provides a novel biological technique with unexpected advantages over the individual components.

According to the invention, two known preparations—HCG and gonadotropin release hormone, GN—RH (synonyms LH—RH, FSH/LH—RH, FSH/LH—RF, LH—RF, Gn—RF and others)—are combined in a ratio between about 1:10 to 10:1, preferably 1:2 to 2:1, and injected or otherwise applied to female livestock, pets, etc. in which a stimulation and/or release of ovulation is desired for either biotechnical or therapeutic reasons. The application should occur early in the mating or spawning cycle or in the period immediately preceding it. For therapy of pathologic states or changes in the organisms, for example, zystose ovary degeneration, a thorough diagnostic evaluation is necessary, so that the injection time corresponds to the desired endocrinological and clinical result. For solution of the preparation, an isotonic medium, e.g. physiological salt solution or serum, is used. The injection may be subcutaneous, intramuscular, intravenous or intraperitonal; preferably, intramuscular injections are carried out. Application with fish can be either through the stomach hole or in the water.

The units of amount and the ratio of the two preparations are with respect to HCG in international units (IE), based on the applicable DDR standards for choriongonadotropin, and for Gn—RH in micrograms ($\mu$g), based on the applicable DDR standards at this time for the preparation VEB Berlinchemie.

The invention may be better understood through the following example.

EXAMPLE

The biotechnical synchronization of ovulation with the use of the preparation combination is illustrated in young and old sows. In the time period shortly before ovulation, young and old sows receive intramuscular injections of the combination. Previously, the ovaries were subjected to a suitable pretreatment, such as Suisynchronpraemix$^R$—Bernburg for young sows. In the case of older sows, the young pigs are removed. In this manner, ripe follicles and egg cells are available. In addition, with animals which go into heat spontaneously, the application may take place in the appropriate interval from the beginning of heat or after diagnostic determination—through hormone analysis, or rectally with cattle.

The treatments were as follows:

Young sows:
1. Suisynchronpraemix for about 15–20 days
2. PMSG (about 1 day after 1.) at about 800–1000 IE
3. Combination according to the invention of about 300 IE HCG and 300 $\mu$g Gn—RH (about 4½ days after 1.)

Older sows:
1. Nursing time of about 4 weeks
2. PMSG (about 1 day after 1.) about 1000–1250 IE
3. Combination of about 300 IE HCG and 3 $\mu$g Gn—RH (about 3½ days after 1.)

With other species, the composition and method may also be used. An injection of the hormone combination to improve the results of insemination is also possible without a presynchronization, if the ovary contains ripe egg follicles and cells; this applies for all species.

Through the use of the inventive hormone combination for ovulation synchronization, a better therapeutic effect is observed than with the previously customary preparations. There follows as well an increase in the fertility results of on average between about 0.4 and 1.0 young pig per insemination. The increase in the fertility results is different between young and old sows; with both, however, the average is increased over the prior art preparations. A further advantage of the inventive hormone combination is a better synchronization of the ovulation time, through which a shortening of the standing time of the sows of about 3 to 4 days is achieved per insemination. This shortening of the standing times leads to corresponding cost reductions.

In addition, through the inventive hormone combination there is achieved a reduction in the amount of HCG used. Through the use of the compositions of the examples, a reduction of about 40% can be achieved. In this manner, the danger of the development of an immunity towards HCG is reduced.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A hormone combination for stimulation of ovulation in female animals, comprising HCG in IE units and Gn—RH in μg in a ratio of 10:1 to 1:10.

2. A hormone combination as defined in claim 1, wherein said ratio is between 2:1 and 1:2.

3. A method for stimulation of ovulation in female animals, comprising administering Gn—RH in μg and HCG in IE units as a combination preparation or separately in a ratio of between 10:1 and 1:10, and preferably 2:1 to 1:2, to animals in heat or during spawning period or immediately prior thereto.

* * * * *